United States Patent [19]
Chapman

[11] Patent Number: 6,148,678
[45] Date of Patent: Nov. 21, 2000

[54] FURNACE WASTE GAS SAMPLING

[75] Inventor: Robert D. Chapman, North Yorkshire, United Kingdom

[73] Assignee: The BOC Group plc, Windlesham, United Kingdom

[21] Appl. No.: 09/315,632

[22] Filed: May 20, 1999

[30] Foreign Application Priority Data

May 20, 1998 [GB] United Kingdom .................... 9810866

[51] Int. Cl.[7] ....................................................... G01N 1/00
[52] U.S. Cl. ......................................................... 73/863.11
[58] Field of Search ............................. 73/863.11, 863.12, 73/863.23, 863.24, 863.41, 863.81, 863.51, 864.81

[56] References Cited

U.S. PATENT DOCUMENTS

| | | | |
|---|---|---|---|
| 4,191,541 | 3/1980 | Jenkins | 73/863.12 |
| 4,481,833 | 11/1984 | Bajek | 73/863.41 |
| 4,779,466 | 10/1988 | Ramsner et al. | 73/863.12 |
| 4,974,455 | 12/1990 | McGowan et al. | 73/863.12 |
| 5,777,241 | 7/1998 | Evenson | 73/863.11 |

FOREIGN PATENT DOCUMENTS 2308649  2/1973  Germany ............................ 73/863.11

*Primary Examiner*—Robert Raevis
*Attorney, Agent, or Firm*—Salvatore P. Pace

[57] ABSTRACT

A probe for analyzing furnace waste gas comprising a water-cooled outer tube containing an inner tube which is not water-cooled and which has a filter at its end. One end of the outer tube is sealed. Waste gas is drawn into the probe through the unsealed end of the outer tube, through the filter and along the inner tube for eventual analysis

15 Claims, 2 Drawing Sheets

FURNACE WASTE GAS SAMPLING

BACKGROUND OF THE INVENTION

This invention relates to the sampling of waste gas (also known as "exhaust gas", or "off-gas") from an industrial furnace, particularly but not exclusively that from an electric arc furnace (EAF). More specifically the invention concerns a probe for carrying out such sampling, and methods relating thereto.

In many industrial furnace operations, and in particular in EAF steelmaking, large volumes of carbon monoxide and/or other combustible gases are evolved during certain parts of the process cycle. These combustible gases form a significant proportion of the waste gas leaving the furnace, along with a normally large amount of particulate dust and liquid or semi-liquid slag droplets.

It is usual to try and burn the combustible gases in the furnace, since this recovers part of the heat content of the gases, and thus saves energy. It also improves the nature of the gases eventually discharged to the environment by destroying toxic gases, and it helps protect downstream waste gas treatment equipment by combusting any explosive gases. To burn the combustible gases, oxygen is lanced into the furnace, and in order to determine the initiation, duration and rate of such oxygen supply it is necessary continuously to analyze the waste gas (by measuring its oxygen or carbon monoxide content, for example) and to use the resulting measurement to open or modulate oxygen admission valves. Because these systems operate on a feedback principle, they must be quick-reacting to any change in the waste gas composition. This means that analysis of the waste gas is carried out on a sample of waste gas drawn from a position as close to the furnace as is practicable, usually at the point where the fixed ducting for drawing the waste gas from the furnace abuts the movable upper section of the furnace. In a typical EAF at this position, the waste gas temperature can reach about 1600° C.

In order to obtain a representative sample of waste gas, the sample is usually drawn from the waste gas flow at a position towards the fastest-flowing part of the waste gas, where the boundary layer effects of the duct walls on the waste gas flow, and its composition, are negligible. This position is generally in the unburned part of the flame caused by the waste gas combustion as it enters the duct from the furnace. The sample is generally obtained by means of a longitudinal probe which is normally inserted vertically downwardly so that its inlet end is located in the above-described position.

The waste gas at the position from which samples are normally taken entrains a high concentration of solid, liquid and semi-liquid contaminants (hereinafter "particulate matter"—slag and the like) which must be separated from the sample of waste gas drawn off before its composition can be analyzed. The particulate matter also impacts on the probe and tends to agglomerate thereon, in particular adjacent the inlet end of the probe, often to the extent that the inlet to the probe becomes blocked, necessitating replacement and/or cleaning of the probe. Particulate matter entrained in the waste gas sample drawn into the probe can also agglomerate inside the probe (at cold spots, or where there is stagnant flow, for example) which again can block the probe. Blockage of the probe, both internal and external, can be exacerbated by the common practice of cooling the probe; it is commonly thought essential to cool the probe, usually with a water cooling system, so as to ameliorate the adverse effects of the high ambient temperature (in the waste gas) on the probe, but cooling the probe can also increase the tendency of molten droplets impacting on the probe to solidify and agglomerate.

The provision of waste gas sampling means which are both capable of delivering a representative sample of waste gas, uncontaminated by entrained particulate matter, for analysis and also not susceptible to blockage by the agglomeration of liquid, semi-liquid and/or solid particulate matter entrained in the waste gas flow is a long-standing problem. It is a particular problem in applications (such as in some EAFs) where there is a large amount of particulate matter entrained in the waste gas flow. Various designs of water cooled probes have been proposed, but none have satisfactorily managed to provide a clean sample of waste gas whilst resisting becoming blocked over an extended period—in most cases, there has been a tendency for blockages to arise, and/or the waste gas analysis to become inaccurate, after only a few days' usage.

SUMMARY OF THE INVENTION

This invention provides apparatus for sampling waste gas flowing along a furnace waste gas duct, comprising an elongate probe for insertion into the duct and comprising an elongate sample tube having an open inlet end through which, in use, waste gas to be sampled is drawn for passage along the tube and out of the duct and a water-cooled elongate extraction conduit surrounding at least a part of the sample tube, the open inlet end of the sample tube being located within the water-cooled elongate extraction conduit, the extraction conduit having an open end through which, in use, waste gas is drawn from the flow of waste gas passing along the duct and an opposite end which is substantially closed to the egress of waste gas, filter means being provided at or adjacent the open inlet end of the sample tube to sieve out entrained particulate matter from the waste gas to be sampled.

Such a "tube in tube" arrangement enables many conventional elements of sample probe design to be adopted for the extraction conduit, whilst providing an enclosure for an inner sample tube which need not itself be water cooled but which can be configured, in relation to the extraction conduit, so as to minimize blockages and also optimize removal of entrained matter in the sample waste gas flow. These advantages derive in part from the entire suction effect for drawing off the waste gas sample being channeled through the sample tube; although the sample waste gas is drawn from the furnace duct into the extraction conduit, there are no means for supplying a suction directly thereto, only those acting on the sample tube, which act indirectly on the extraction conduit.

A further important aspect of this invention concerns the location of the filter means. Whilst filters have been used in sample probes in the past, by and large these have been unsuccessful because they have been prone to blockage, or have required overly complicated purging arrangements to clear them of particulate matter accumulated in the filter during use. A contributory factor to the blockage of the filter occurs when the temperature of the waste gas flowing through the filter passes through the dew point temperature whilst still within the filter; as the waste gas cools beyond the dew point temperature, condensation occurs which wets the filter and exacerbates the blocking effect of accumulated particulate matter.

So, in any waste gas sample probe in which, in use, a decreasing waste gas temperature profile is established and in which a filter is used, the filter is located relative to the temperature profile such that the entire filter is maintained at a temperature above the dew point temperature of the waste gas.

Those skilled in the art will appreciate that the concept of maintaining the filter above the dew point temperature is applicable independently of the first aspect of the invention described above. In any event, condensation of the waste gas in the portions of the waste gas sampling system is nearly as undesirable as condensation in the filter, however such condensation is prevented by the simple and conventional expedient of heating the sample tube which directs the sample waste gas from the probe to the waste gas analysis apparatus.

The sample tube is preferably movable relative to the extraction conduit, such that the position of the filter means relative to the open and closed ends of the extraction conduit can be adjusted. This enables the filter means to be maintained in a position where it is above the waste gas dew point temperature, should the furnace operating conditions charge, the probe be moved or transferred to a different furnace.

It is advisable that means be provided for sensing the waste gas temperature along at least a part of the distance between the open and closed ends of the extraction conduit. This can be conveniently embodied as a thermocouple, which is movable along the extraction conduit so as to establish the location therein where the waste gas reaches the dew point temperature.

Notwithstanding that the extraction conduit is of course configured so as to draw in the minimum amount of particulate matter entrained in the waste gas and the filter, in practice the filter means will eventually become loaded with particulate matter which requires cleaning off so that the filter means and the apparatus can function efficiently. This may be achieved using a purging system in which compressed air (or any other gas) is blown through and over the filter means (for efficiency this is usually in a direction contrary to that of the flow of waste gas through and over the filter means in use). Compressed air may be introduced into the sample tube, to blow back through the filter means and eject accumulated particulate material therefrom. Additionally or alternatively, compressed air may be introduced into the extraction conduit to pass over the surface of the filter means in order to remove particulate mater. Conveniently the compressed air is introduced through the sealed end of the extraction conduit. Where the extraction conduit and sample tube adopt a concentric cylindrical "tube in tube" configuration, a disc may be affixed to the sample tube so as to leave a thin annulus between the disc circumference and the inner wall through which the compressed air can flow; this both directs the flow of compressed air so that it passes over the maximum amount of surface of the filter means, and also accelerates it so as to increase its efficacy in removing particulate matter from that surface. Those with even only a rudimentary knowledge of fluid mechanics will appreciate how such an arrangement can be adapted for any configuration of sample probe, and to take account of such other factors as temperature, type of particulate matter, type and configuration of filter means, purging gas and the like.

It will be apparent that the invention also encompasses methods of use of the apparatus described above. As is usual the probe is located within the waste gas duct such that the open end of the extraction conduit is disposed away from the walls defining the duct and toward the region in the duct where the waste gas flow is fastest. Then, suction is applied to the sample tube, so as to draw waste gas into the extraction conduit open end, through the filter means, and into the sample tube for onward transmission to the gas analysis equipment. As is usual, the probe is positioned so that it is vertically orientated with the extraction conduit open end lowermost, the temperature profile of the waste gas within the extraction conduit established so that the filter means can be moved so that, temperature-wise, it is above the waste gas dew point temperature (but, location-wise, below the point at which the sample waste gas reaches its dew point temperature).

DETAILED DESCRIPTION OF THE INVENTION

Figure 1:
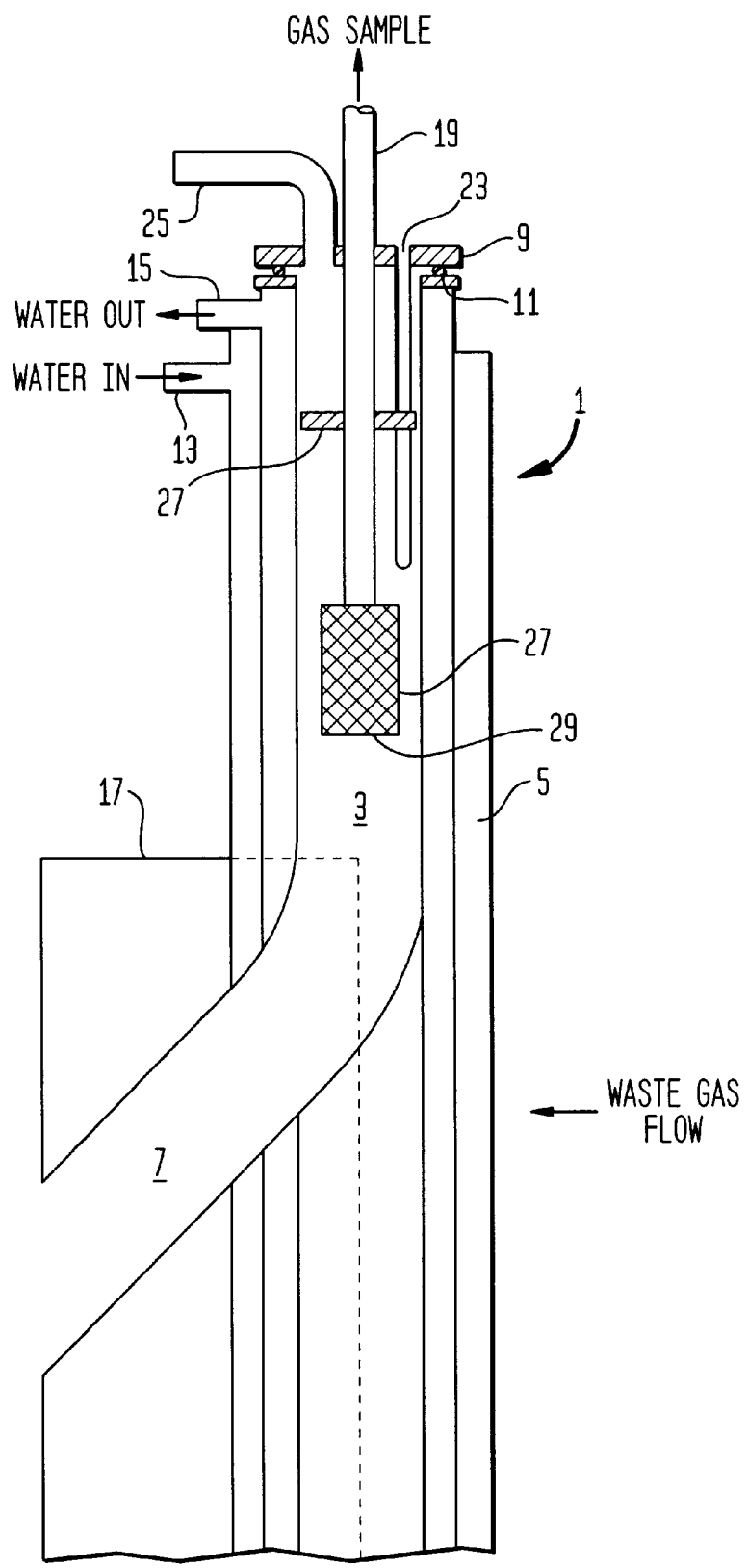
FIG. 1 is a schematic cross-sectional side elevation of an embodiment of a waste gas sample probe in accordance with the invention.
Figure 2:
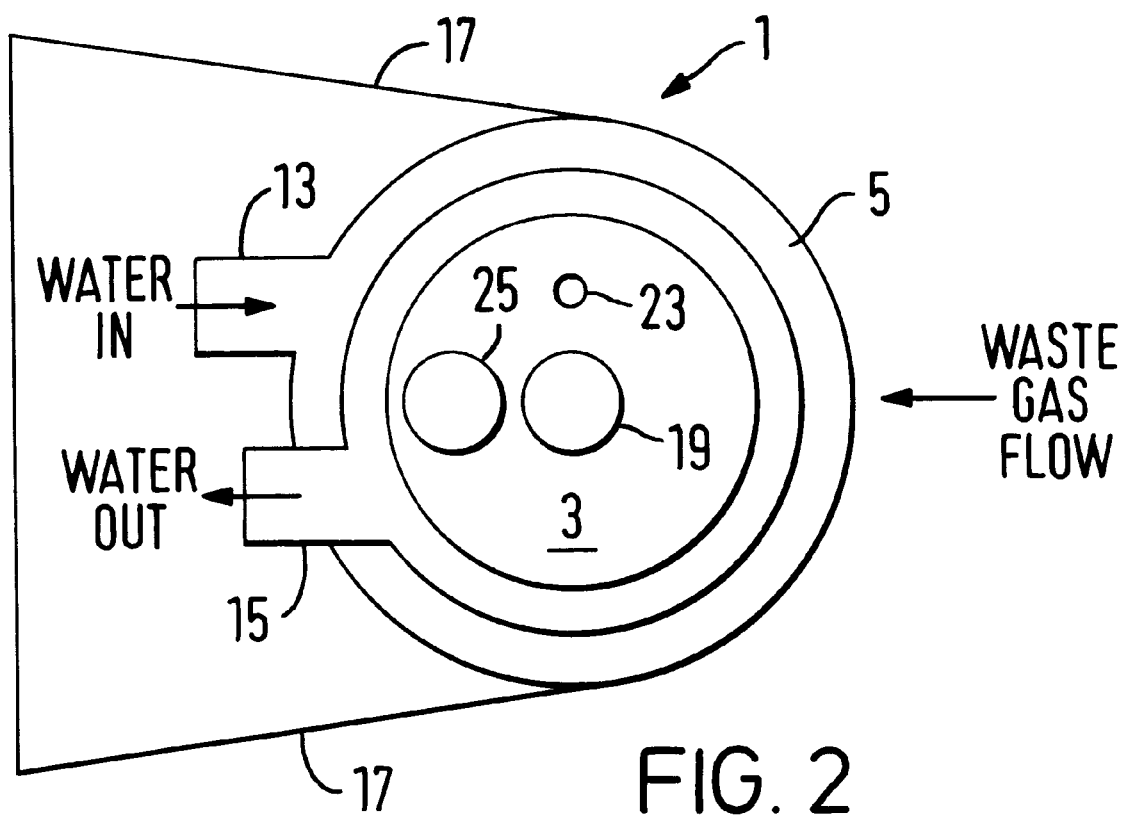
FIG. 2 is a schematic plan view of the probe of FIG. 1.

The waste gas sample probe 1 shown schematically in FIGS. 1 and 2 is adapted for substantially vertical location within the waste gas ductwork (not shown) of an electric arc furnace (not shown) and closely adjacent thereto. In order to withstand the fierce temperature and aggressive atmosphere, probe 1 is largely made of stainless steel, and comprises an extraction conduit 3 enclosed within a water-cooled jacket 5. Conduit 3 is open at one end 7 for the ingress of waste gas to be sampled, and closed at the other, upper end by a lid 9 (an 'O' ring seal or the like being provided to ensure a gas tight closure). Jacket 5 is provided with an inlet 13 and an outlet 15 for the circulation of water (or any other suitable coolant) to cool the probe 1 in use—as is well known in the art.

Although largely cylindrical, the lower end of probe 1 is aerodynamically profiled by means of slag deflector plates 17, so that in use conduit open end 7 is in the lee of the waste gas flow; this ensures that when waste gas is drawn into the open end 7 to be sampled a minimum of entrained matter reverses direction so as to be drawn into the conduit 3.

A movable sample tube 19 is located within conduit 3 and has a filter 21, such as a comercially-available sintered metal fiber filter attached at its lower end, within the conduit 3. The sample tube 19 extends through the lid 9 and towards the equipment for analyzing the composition of the waste gas (not shown) and incorporates conventional (and so not shown) heating means (to prevent sample waste gases condensing prior to analysis) and condenser means (to remove water from the sample waste gas—also not shown). A magnet 29 is mounted lower end of the filter 21, and is effective to prevent ferro-magnetic particles from reaching the filter 21; magnet 29 is preferably an electromagnet, so that it can periodically be cleaned.

In use, suction is applied to the sample tube 19 from outside the waste gas ductwork, which draws a sample of waste gas from the main waste gas flow into the open end 7 of the extraction conduit 3, through the filter 21 and into and along the sample tube 19. The shape and configuration of the probe 1 and of the extraction conduit 3 (which has a marked but smooth bend so as to draw sample waste gas almost horizontally from the leeward side of the probe 1 before drawing it upwardly, thus helping separate out entrained particulate matter from the sample waste gas) are designed to minimize the amount of entrained particulate matter transmitted along the sample tube 19. Locating the open end 7 of the conduit 3 to the leeward side of the probe 1 in the main waste gas flow reduces the amount of particulate matter entrained in the waste gas flow which is drawn into the probe 1. Of the entrained particulate matter drawn into the probe 1, much settles out due to the vertical orientation of the path to the sample tube 19, to settle in the areas of the conduit 3 where the flow is stagnant—such as in the region above the filter towards the lid 9. Ferro-magnetic particles are attracted and adhere to the magnet 21. Any remaining particulate matter is sieved out of the sample waste gas flow by the filter 21 before the sample waste gas passes out of the probe.

Because of the water-cooling jacket 5, the temperature of the waste gas in the conduit 3 decreases as the gas moves vertically upwards, i.e., there is a decreasing temperature profile in that direction. So as to prevent blocking of the filter 21 due to condensation, the filter 21 is moved to a position at which the waste gas temperature within the conduit 3 is above its dew point temperature. Viewed physically, the filter 21 is located below the level in the conduit 3 at which the sample waste gas is cooled by the water jacket 5 to the dew point temperature. Movement of the filter 21 up and down the vertical portion of the conduit is possible, and the location of the level of the dew point temperature is by means of a thermocouple (not shown), which is insertable in thermocouple pocket 23 extending down the conduit 3.

Over time, the filter 21 becomes laden with accumulated particulate matter. The filter 21 can be cleaned by blasting a high pressure burst of purge gas (usually compressed air) down the sample tube 19. Purge gas can also be supplied through pipe 25, which passes through lid 9, to remove particulate matter from the outer surface of the filter 21. A disc 27 fixed to the sample tube 19 and providing only a small clearance (typically about 1 mm—although not to scale, the inside diameter of conduit 3 shown in the drawings would be about 50 mm) between its circumference and the wall of conduit 3 directs the flow of purge gas evenly around the surface of the filter 21 and accelerates said flow so as to improve its efficacy in scouring particulate matter from the surface region of the filter 21.

During this purging, magnet 21 can be de-magnetized so as to remove ferro-magnetic particles adhering thereto.

Those skilled in the art will appreciate that there are many quite straightforward modifications (not shown) which could be incorporated into the apparatus shown in the figures. Water heating means could be provided for the sample tube 19 leading away from the probe 1, and temperature sensing means (such as further thermocouples) could be provided for the water entering and leaving inlet 13 and outlet 15, so that the flow of cooling water may be varied as necessary to optimize the probe's performance, and means could be provided so as automatically to control the flow of coolant in response to the sensed temperatures. The cross-sectional area of the conduit 3, although shown as constant, could be varied so as to accelerate or decelerate the flow of gas therealong in a bid to prevent entrained particulate matter being drawn into the conduit and/or towards the filter 21. Additional magnetic means could be provided to separate entrained ferro-magnetic particulate matter from the sample waste gas in the conduit 3, such as powerful electro magnetic means located within the water-cooled jacket, for example. Means, such as vane arrangements, could provide a cyclonic flow of the purge gas (which could be other than air) scouring the surface of the filter 21.

Finally, to avoid misapprehension, whenever the words "comprises" or "comprising" are employed herein, in the description, claims or abstract, they are not to be construed as comprehensive or exhaustive; that is to say, the words are always to be read and construed as if preceded by the term "inter alia". It will be apparent to those skilled in the art that various modifications and variations can be made to the methodology of the present invention without departing from the scope or spirit of the invention. In view of the foregoing, it is intended that the present invention cover modifications and variations of this invention provided they fall within the scope of the following claims and their equivalents.

I claim:

1. An apparatus for sampling waste gas flowing along a furnace waste gas duct, comprising an elongate probe for insertion into the duct and comprising an elongate sample tube having an open inlet end through which waste gas to be sampled is drawn for passage along the tube and out of the duct and a water-cooled elongate extraction conduit surrounding at least a part of the sample tube, the open inlet end of the sample tube being located within the water-cooled elongate extraction conduit, the extraction conduit having an open end through which waste gas is drawn from the flow of waste gas passing along the duct and an opposite end which is substantially closed to the egress of waste gas, filter means being provided at or adjacent the open inlet end of the sample tube to sieve out entrained particulate matter from the waste gas to be sampled, means for sensing the waste gas temperature along at least a part of the distance between the open and closed ends of the elongate extraction conduit, wherein a decreasing temperature profile is established in the waste gas between the open and closed ends of the elongate extraction conduit, the sample tube being located in relation thereto such that the filter means is maintained at a temperature above the dew point temperature of the waste gas.

2. The apparatus according to claim 1 wherein the sample tube is movable relative to the extraction conduit, such that the position of the filter means relative to the open and closed ends of the extraction conduit can be adjusted.

3. The apparatus according to claim 1 further comprising means for sensing the waste gas temperature along at least a part of the distance between the open and closed ends of the extraction conduit.

4. The apparatus according to claim 1 further comprising purge means for intermittently clearing the filter means of accumulated particulate matter.

5. The apparatus according to claim 4 wherein the purge means comprises means for introducing compressed air into the sample tube.

6. The apparatus according to claim 4 wherein the purge means comprises means for introducing compressed air into the extraction conduit at or adjacent the closed end thereof.

7. The apparatus according to claim 6 comprising means disposed between the point of introduction of compressed air into the extraction conduit and the filter means and adapted to direct the flow of compressed air substantially evenly over the filter means.

8. The apparatus according to claim 1 wherein the opened end of the extraction conduit is located within an inlet head, the inlet head being aerodynamically profiled such that, in use, liquid, semi-liquid or particulate matter entrained in the waste gas flow and impacting thereon is clearly detached therefrom by the flow of waste gas thereby.

9. The apparatus according to claim 8 wherein the aerodynamic profile has a trailing end and wherein the open end of the extraction conduit is located at the trailing end.

10. The apparatus according to claim 1 wherein the elongate extraction conduit has an inlet section adjacent the open end, which section is not parallel to the axis of the remainder of the extraction conduit.

11. The apparatus according to claim 10 wherein the inlet and remaining sections of the extraction conduit are configured so as to provide a smooth passage for waste gas passing from the open end of the extraction conduit to the filter means.

12. A method for sampling waste gas flowing along a furnace waste gas duct, comprising the steps of inserting an elongate probe into the duct said probe having an elongate sample tube having an open inlet end through which waste gas to be sampled is drawn for passage along the tube and out of the duct and a water-cooled elongate extraction conduit surrounding at least a part of the sample tube, the open inlet end of the sample tube being located within the water-cooled elongate extraction conduit, the elongate extraction conduit having an open end through which waste gas is drawn from the flow of waste gas passing along the duct and an opposite end which is substantially closed to the egress of waste gas, providing filter means at or adjacent the open inlet end of the sample tube to sieve out entrained particulate matter from the waste gas to be sampled, determining the waste gas temperature along at least a part of the distance between the open and closed ends of the elongate extraction conduit, and locating the sample tube there within such that the filter means is maintained at a temperature above the dew point temperature of the waste gas.

13. The method of claim 12 further comprising the step of locating the probe within the waste gas duct such that the open end of the extraction conduit is disposed away from the walls defining the duct and toward the region in the duct where the waste gas flow is fastest.

14. The method according to claim 13 wherein the probe is disposed substantially vertically, with the extraction conduit open end lowermost.

15. The method according to claim 13 further comprising the step of drawing a sample of waste gas into the open end of the extraction conduit and, via the filter means, into the open inlet end of the sample tube for passage therealong to means for analyzing the composition of the sample waste gas.

* * * * *